(12) United States Patent
Lin et al.

(10) Patent No.: US 10,639,264 B2
(45) Date of Patent: May 5, 2020

(54) MESENCHYMAL STEM CELL EXTRACT AND ITS USE

(71) Applicant: GWO XI STEM CELL APPLIED TECHNOLOGY CO., LTD., Hsinchu County (TW)

(72) Inventors: Shinn-Zong Lin, Hsinchu County (TW); Horng-Jyh Harn, Hsinchu County (TW); Tzyy-Wen Chiou, Hsinchu County (TW); Po-Cheng Lin, Hsinchu County (TW)

(73) Assignee: GWO XI STEM CELL APPLIED TECHNOLOGY CO., LTD., Zhubei, Hsinchu County (TW)

( * ) Notice: Subject to any disclaimer, the term of this patent is extended or adjusted under 35 U.S.C. 154(b) by 16 days.

(21) Appl. No.: 15/980,184

(22) Filed: May 15, 2018

(65) Prior Publication Data

US 2018/0250216 A1    Sep. 6, 2018

Related U.S. Application Data

(62) Division of application No. 14/321,954, filed on Jul. 2, 2014, now Pat. No. 10,022,313.

(30) Foreign Application Priority Data

Feb. 17, 2014 (TW) .............................. 103105080 A

(51) Int. Cl.
| | |
|---|---|
| *A61K 8/64* | (2006.01) |
| *A61K 8/98* | (2006.01) |
| *A61Q 7/00* | (2006.01) |
| *A61Q 19/08* | (2006.01) |
| *A61F 7/02* | (2006.01) |
| *A61F 7/00* | (2006.01) |
| *A61N 5/06* | (2006.01) |

(52) U.S. Cl.
CPC ................ *A61K 8/64* (2013.01); *A61K 8/981* (2013.01); *A61Q 7/00* (2013.01); *A61Q 19/08* (2013.01); *A61F 7/02* (2013.01); *A61F 2007/0003* (2013.01); *A61F 2007/0062* (2013.01); *A61F 2007/0088* (2013.01); *A61K 2800/805* (2013.01); *A61K 2800/86* (2013.01); *A61K 2800/88* (2013.01); *A61N 5/0625* (2013.01)

(58) Field of Classification Search
None
See application file for complete search history.

(56) References Cited

U.S. PATENT DOCUMENTS

| | | | | |
|---|---|---|---|---|
| 2007/0065415 | A1* | 3/2007 | Kleinsek | A61K 35/12 424/93.7 |
| 2007/0292401 | A1* | 12/2007 | Harmon | A61K 35/28 424/93.21 |
| 2010/0217357 | A1 | 8/2010 | Da Silva et al. | |
| 2011/0300102 | A1 | 12/2011 | Chung et al. | |
| 2013/0096064 | A1 | 4/2013 | Chandler | |

FOREIGN PATENT DOCUMENTS

| | | |
|---|---|---|
| CN | 101237898 | 8/2008 |
| CN | 102333523 | 1/2012 |

OTHER PUBLICATIONS

U.S. Appl. No. 14/321,954, filed Jul. 2, 2014, Pending.
Dai, H. Y. et al., "Extraction methods optimization in high-field MRS study of the human umbilical cord mesenchymal stem cells", Chin J Magn Reson Imaging, 2011, vol. 2(6), pp. 430-434.
Yang, J. A. et al., "Potential application of adipose-derived stem cells and their secretory factors to skin: discussion from both clinical and industrial viewpoints", Expert Opin Biol Ther., 2010, vol. 10(4), ppl. 495-503.
Xu, Q,Y., "Change in CXCR4 expression on aged bone marrow cell, and the effect on regeneration of blood vessel caused thereby" Zhejiang University, Mar. 1, 2010, pp. 1-2.
Safety and Technical Standards for Cosmetics, 2015.
File History of U.S. Appl. No. 14/321,954, filed Jul. 2, 2014.

* cited by examiner

*Primary Examiner* — Nghi V Nguyen
(74) *Attorney, Agent, or Firm* — Ping Wang; Morris, Manning & Martin, LLP

(57) ABSTRACT

A mesenchymal stem cell extract and its use are provided, wherein the mesenchymal stem cell extract comprises a trophic factor(s), such as bone morphogenetic protein-7 (BMP-7), stromal cell-derived factor-1 (SDF-1), vascular endothelial growth factor (VEGF), C-X-C chemokine receptor type-4 (CXCR4), brain-derived neurotrophic factor (BDNF), and/or interleukin-17 (IL-17), and wherein the extract is especially suitable for repairing skin aging.

5 Claims, 7 Drawing Sheets
(6 of 7 Drawing Sheet(s) Filed in Color)
Specification includes a Sequence Listing.

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: BMP-7 primer- Forward Sequence

<400> SEQUENCE: 1
ggctggcagc actggatcat                                              20

<210> SEQ ID NO 2
<211> LENGTH: 20
<212> TYPE: DNA
<213> ORGANISM: Artificial Sequence
<220> FEATURE:
<223> OTHER INFORMATION: BMP-7 primer-  Reverse Sequence

<400> SEQUENCE: 2
accagcgtct gcacgatggc                                              20

<210> SEQ ID NO 3
<211> LENGTH: 21
<212> TYPE: DNA
<213> ORGANISM: Artificial Sequence
<220> FEATURE:
<223> OTHER INFORMATION: SDF-1 primer- Forward Sequence

<400> SEQUENCE: 3
atgaacgcca aggtcgtggt c                                            21

<210> SEQ ID NO 4
<211> LENGTH: 26
<212> TYPE: DNA
<213> ORGANISM: Artificial Sequence
```

```
<220> FEATURE:
<223> OTHER INFORMATION: SDF-1 primer- Reverse Sequence

<400> SEQUENCE: 4
cttgtttaaa gctttctcca ggtact                                          26

<210> SEQ ID NO 5
<211> LENGTH: 20
<212> TYPE: DNA
<213> ORGANISM: Artificial Sequence
<220> FEATURE:
<223> OTHER INFORMATION: CXCR4 primer- Forward Sequence

<400> SEQUENCE: 5
ggccctcaag accacagtca                                                 20

<210> SEQ ID NO 6
<211> LENGTH: 23
<212> TYPE: DNA
<213> ORGANISM: Artificial Sequence
<220> FEATURE:
<223> OTHER INFORMATION: CXCR4 primer- Reverse Sequence

<400> SEQUENCE: 6
ttagctggag tgaaaacttg aag                                             23

<210> SEQ ID NO 7
<211> LENGTH: 21
<212> TYPE: DNA
<213> ORGANISM: Artificial Sequence
<220> FEATURE:
<223> OTHER INFORMATION: IL-17 primer- Forward Sequence

<400> SEQUENCE: 7
tccaccgcaa tgaggaccct g                                               21

<210> SEQ ID NO 8
<211> LENGTH: 20
<212> TYPE: DNA
<213> ORGANISM: Artificial Sequence
<220> FEATURE:
<223> OTHER INFORMATION: IL-17 primer- Reverse Sequence

<400> SEQUENCE: 8
tgacacaggt gcagcccacg                                                 20

<210> SEQ ID NO 9
<211> LENGTH: 18
<212> TYPE: DNA
<213> ORGANISM: Artificial Sequence
<220> FEATURE:
<223> OTHER INFORMATION: -actin primer- Forward Sequence

<400> SEQUENCE: 9
cgccaaccgc gagaagat                                                   18

<210> SEQ ID NO 10
<211> LENGTH: 19
<212> TYPE: DNA
<213> ORGANISM: Artificial Sequence
<220> FEATURE:
<223> OTHER INFORMATION: -actin primer- Reverse Sequence

<400> SEQUENCE: 10
cgtcaccggg agtccatca                                                  19
```

MESENCHYMAL STEM CELL EXTRACT AND ITS USE

This application is a Divisional of U.S. application Ser. No. 14/321,954, filed Jul. 2, 2014, which claims priority to Taiwan Patent Application No. 103105080 filed on Feb. 17, 2014, in the Taiwan Intellectual Property Office, the disclosure of which is incorporated herein in its entirety by reference.

FIELD

The present invention relates to an extract of a mesenchymal stem cell (MSC) and the use thereof. In particular, the present invention relates to a use of the extract in repairing skin aging, especially in promoting the expression of hyaluronic acid, elastin, collagen and/or reticulin in the skin, stimulating cell proliferation at the administered region, stimulating cells at the administered region to secrete a trophic factor, and/or stimulating endogenous hematopoietic progenitor cells to gather and proliferate at the administered region. The mesenchymal stem cell extract of the present invention can be used in combination with a heating means to provide an excellent effect on repairing skin aging.

BACKGROUND

The skin, which covers the surface of the human body, is the largest organ of the human body. The skin protects the human body, responds to sensation, and regulates the human body temperature. The structure of the skin, from most superficial to least superficial, includes the epidermis, dermis, and hypodermis. In general, skin aging increases with age. There are two classifications of factors that cause skin aging: endogenous and exogenous. Endogenous aging is a natural aging process of the human body. The following are just some of the ways endogenous aging may affect the skin. The keratinocyte stem cells decrease along with increase in age which may cause the disorders of cells in the basal layer and the decrease of hyaluronic acid and moisturizing factors. In addition, the decrease of hormone (such as sebaceous glands) secretion may slow the metabolism of the skin, and thus, leads to a loss of tension and elasticity of the skin. The deterioration of the functions of fibroblasts in the dermis may also slowly decrease the production of collagen and elastin, thus, causes the connective tissue in the dermis to degenerate, leading to flaccidity and even wrinkling of the skin. The degeneration of connective tissues in the dermis may decrease the water storage function of the skin, leading to skin dryness and water deficiency. Lastly, the atrophy of epidermis and dermis may decrease the protective ability of the skin, or lead to a loss of elasticity of the blood vessels and result in subcutaneous hemorrhages.

Exogenous aging is caused by the direct contact between the skin and the environment, in which the skin is exposed to extrinsic factors, such as sunshine, pollution, free radicals, and smoking. Exogenous aging of the skin includes the inhibition of cellular renewal and repair, decrease in protective ability, and the accumulation of melanin. The main factor that causes skin aging is damage caused by ultraviolet (UV) rays from the sun, which may accelerate skin aging by 5 to 10 times. Long wavelength UV (UVA) and medium wavelength UV (UVB) are the most common UV rays in daily life. Long-term exposure to UVB may stimulate fibroblasts in the dermis to express collagenases to degrade collagen, thus, leads to a decrease of collagen density, a denaturation of collagen, and a loss of elasticity of the skin. In addition, the melanocytes will start to degenerate, leading to uneven color in the skin. As a result, free radicals are overly generated in the skin, leading to the formation of skin darkness and dark spots, and even various cutaneous carcinomas.

To date, there are many methods for preventing and repairing skin aging, including extracellular matrix (ECM) supplement therapy, *Clostridium botulinum* injection, and exfoliative physiotherapy. The ECM supplement therapy includes applying collagen, elastin, hyaluronic acid or vitamin E onto the surface of the skin. However, the structure of these molecules is too big to be absorbed effectively by the skin and get into the dermis layer. The therapeutical effect of ECM supplement therapy is limited because these molecules cannot be maintained in the human body for over 9 months. Though *Clostridium botulinum* injection can improve skin flaccidity, its effect can only be maintained for 3 to 6 months and it may cause side effects, such as upper eyelid ptosis, rigid and strange facial expression, or muscle weakness at the injected region. Though exfoliative physiotherapy can remove aged horniness and stimulate skin proliferation, there are many side effects, including weakened skin, slow repair and many postoperative complications.

Cellular therapy is another option for treating skin aging, which comprises the use of stem cells to improve the damaged skin tissue. For example, an adipose-derived stem cell (ADSC) is a multipotent stem cell separated from fat tissue, similar to an umbilical cord stem cell, and is one kind of human mesenchymal stem cell. ADSCs are highly plastic and can be classified into various histocytes, such as neural cells, vascular endothelial cells, cardiocytes, hepatocytes, chondrocytes, and myocytes. Formerly, most of the fat tissue obtained from liposuction surgery was thrown away as waste. However, researches have found that fat tissue is rich in mesenchymal stem cells, which have the potential of external proliferation and multiple differentiations, and thus can be used in the renewal and repair of tissues and organs. These cells can be acquired with low invasiveness and with less harm to the human body. In addition, these cells can be cultured in vitro and can be widely used in various types of body tissues. These cells can move to the wounded regions spontaneously and repair the wounds.

Currently, cellular therapy must be conducted by injecting the cells into a subject. The most common way to inject a certain amount of stem cells is subcutaneously. However, this therapy is invasive and carries some risks, and will cause many traumatic wounds that may affect the appearance of the skin. Furthermore, the application of such a traditional cellular therapy has many limitations because living cells are used in this therapy, the safety of the living cells should be evaluated strictly before injection, and when applied to humans, the living cells should originate from human stem cells.

In view of the limited efficacy and side effects of the above ECM supplement therapy and *Clostridium botulinum* injection and the potential risks and limitations of the cellular therapy, there is still a need for an effective and simple method for repairing skin aging.

The present invention provides an extract extracted from mesenchymal stem cells for resolving the above issues. The mesenchymal stem cell extract can be applied topically and get into the human body, to promote the expression of hyaluronic acid, elastin, collagen and/or reticulin in the skin, stimulate cell proliferation at the administered region, stimulate cells at the administered region to secrete a trophic factor, and stimulate endogenous hematopoietic progenitor cells (HPC) to gather and proliferate at the administered region. The mesenchymal stem cell extract can be used in combination with a heating means to provide an excellent effect of repairing skin aging.

SUMMARY

An objective of the present invention is to provide a mesenchymal stem cell extract, comprising a trophic factor selected from the group consisting of bone morphogenetic protein-7 (BMP-7), stromal cell-derived factor-1 (SDF-1), vascular endothelial growth factor (VEGF), C-X-C chemokine receptor type-4 (CXCR4), brain-derived neurotrophic factor (BDNF), interleukin-17 (IL-17), and combinations thereof.

Another objective of the present invention is to provide a use of the aforesaid mesenchymal stem cell extract in the manufacture of a skincare product, a cosmetic or a medicament.

Yet another objective of this invention is to provide a kit, comprising the aforesaid mesenchymal stem cell extract and a heating tool.

Yet another further objective of this invention is to provide a method for repairing skin aging in a subject in need, comprising administering to the subject an effective amount of the aforesaid mesenchymal stem cell extract, and optionally heating the skin surface of the subject with a heating means prior to, simultaneously with, and/or after the administration of mesenchymal stem cell extract.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
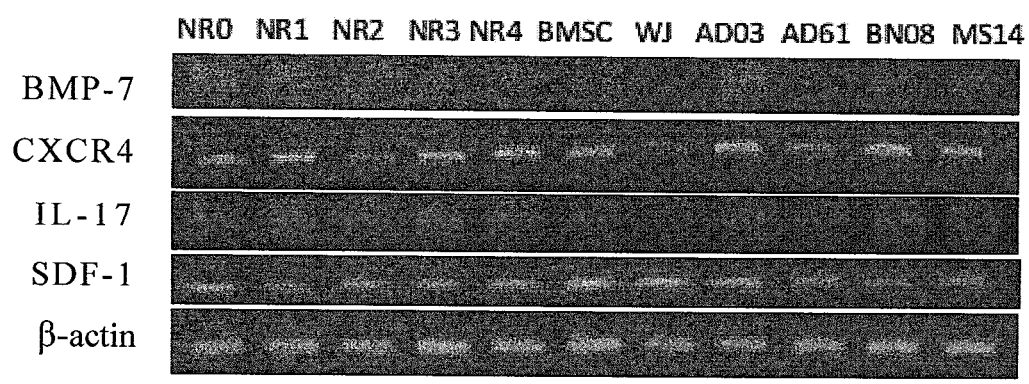
FIG. 1 is an electrophoresis photograph showing the expression level of trophic factors in mesenchymal stem cells according to an embodiment of the present invention.

The following will describe some embodiments of the present invention in detail. However, without departing from the spirit of the present invention, the present invention may be embodied in various embodiments and should not be limited to the embodiments described in the specification. In addition, unless otherwise indicated herein, the expressions "a," "the," or the like recited in the specification of the present invention (especially in the claims) are intended to include the singular and plural forms. Furthermore, the term "effective amount" or "amount effective for treatment" used in this specification refers to the amount of the extract that can at least partially alleviate the condition that is being treated in a suspected subject when administered to the subject. The term "subject" used in this specification refers to a mammalian, including human and non-human animals.

The present invention provides a mesenchymal stem cell extract, comprising a trophic factor selected from the group consisting of bone morphogenetic protein-7 (BMP-7), stromal cell-derived factor-1 (SDF-1), vascular endothelial growth factor (VEGF), C-X-C chemokine receptor type-4 (CXCR4), brain-derived neurotrophic factor (BDNF), interleukin-17 (IL-17), and combinations thereof.

The mesenchymal stem cell extract of the present invention was obtained by extracting mesenchymal stem cells separated from an animal tissue. That is, the mesenchymal stem cell extract can be provided by directly extracting the mesenchymal stem cells separated from an animal tissue, or be provided by extracting the mesenchymal stem cells generated from the cultivation of the mesenchymal stem cells separated from an animal tissue. Suitable tissues include, for example, umbilical cord, umbilical cord blood, placenta, Wharton's jelly (WJ), bone marrow (BM), blood, muscle, fat, follicle, and combinations thereof. In some embodiments of the present invention, a mesenchymal stem cell extract obtained by extracting mesenchymal stem cells originated from fat tissue was used.

The mesenchymal stem cells directly separated from an animal tissue may be produced autologously, or produced by an exogenous induction. For example, when use mesenchymal stem cells separated from bone marrow or blood, the mesenchymal stem cells may be produced autologously, or induced by a granulocyte colony stimulating factor (GCSF) and/or an interleukin. For example, the GCSF and interleukin used for induction may be an endogenous GCSF and interleukin, synthetic GCSF and interleukin, and/or analogues thereof. In addition, the interleukin used for induction may be interleukin-3 (IL-3) and/or interleukin-6 (IL-6).

The mesenchymal stem cell extract of the present invention can be prepared by any suitable method. For example, the mesenchymal stem cell extract can be provided by extracting mesenchymal stem cells originated from an animal tissue with the use of a proteolysis buffer. In some embodiments of the present invention, the mesenchymal stem cell extract was provided by the following steps:

(1) mixing mesenchymal stem cells with a proteolysis buffer containing NP40 lysis buffer, phenylmethanesulfonyl fluoride (PMSF), a protease inhibitor, β-glycerol phosphate and $Na_3VO_4$, to lyse the cells and provide a cell lysate; and (2) centrifuging the cell lysate to collect the supernatant (i.e., a mesenchymal stem cell extract), wherein, to avoid the inactivation of effective components in the extract, the centrifugation is preferably performed at a temperature below 4° C. to maintain the stability of the effective components.

Because the mesenchymal stem cell extract of the present invention is extracted from cells, the molecular structure of the effective components (comprising at least one of BMP-7, SDF-1, VEGF, CXCR4, BDNF, and IL-17) in the extract is small, and thus, can easily penetrate the skin while being applied to the skin surface to promote the expression of hyaluronic acid, elastin, collagen and/or reticulin in the skin, stimulate cell proliferation at the administered region, stimulate cells at the administered region to secrete a trophic factor, and/or stimulate endogenous hematopoietic progenitor cells to gather and proliferate at the administered region.

Without being limited by theory, it is believed that the mesenchymal stem cell extract of the present invention is effective in repairing skin aging, which comprises, but are not limited to, promoting wound healing, improving the skin quality (such as the thickness, elasticity, flexibility, fullness and humidity of the skin) and skin flaccidity, reducing skin wrinkles and stripes, improving skin firmness, whitening the skin, and reducing skin darkness and skin spots. In addition, the mesenchymal stem cell extract of the present invention can effectively reduce hair loss, promote the activation of hair follicle cells, promote the proliferation of hair follicle cells, and/or promote hair growth.

The inventors of the present invention found that when the skin surface is heated with a heating means prior to, simultaneously with, and/or after the administration of the mesenchymal stem cell extract of the present invention, the heating operation can open the skin pores and thereby, increase the absorption efficiency, stimulate the release of trophic factors, attract endogenous stem cells to migrate to the administered region, and repair and increase the ECM, so as to achieve the effect of skin rejuvenation.

Accordingly, the present invention also relates to applications of the mesenchymal stem cell extract for repairing skin aging, including a use of the mesenchymal stem cell extract in the manufacture of a skin care product, a cosmetic or a medicament for repairing skin aging, a kit comprising the mesenchymal stem cell extract and a heating means, and a method for repairing skin aging in a subject in need comprising administering to the subject the mesenchymal stem cell extract.

The skin care products, cosmetics and medicaments of the present invention can be presented in any suitable form without particular limits. For example, the skin care products, cosmetics and medicaments can be in the form of an emulsion, a cream, gel (such as an aquagel), paste (such as a dispersing paste and an ointment), a spray or a solution (such as a washing liquid and a suspension) for external use, but are not limited thereby. The skin care products of the present invention can also be prepared in the form of a food for swallowing or drinking, such as a health food or a beauty drink. In addition, the medicaments of the present invention can be prepared in the form for oral administration or subcutaneous injection.

When the medicament manufactured by using the mesenchymal stem cell extract of the present invention is in the form for oral administration, the medicament may comprise any pharmaceutical acceptable carrier which would not adversely influence the desired activity of the mesenchymal stem cell extract. Examples of a suitable pharmaceutical acceptable carrier include, but are not limited to solvents, oily solvents, diluents, stabilizers, absorption retarders, disintegrants, emulsifiers, antioxidants, adhesives, lubricants, moisture absorbents, etc. Any suitable methods can be used to prepare the medicament in an oral administration form such as a tablet, a capsule, a granule, a powder, a fluid extract, a solution, syrup, a suspension, an emulsion, a tincture, etc.

When the medicament manufactured by using the mesenchymal stem cell extract of the present invention is in the form for subcutaneous injection, the medicament may comprise one or more component(s), such as an isotonic solution, a saline buffer solution (such as a phosphate buffer solution or a citrate buffer solution), a solubilizer, an emulsifier, other carriers, etc., so as to be manufactured as a powder injection, a suspension injection, or a powder-suspension injection.

Optionally, the skin care product, cosmetic, or medicament manufactured by using the mesenchymal stem cell extract of the present invention can further comprise other additives, such as a flavoring agent, a perfume, a toner, or a coloring agent to enhance the taste and visual appeal of the skin care product, cosmetic or medicament. A suitable amount of a preservative, a conservative, an antiseptic, an anti-fungus reagent, and so on, can also be added to improve the storability of the skin care product, cosmetic or medicament. In addition, the skin care product, cosmetic or medicament can be optionally used in combination with one or more other active components to further enhance the efficacy of the skin care product, cosmetic or medicament, or to increase the flexibility for the formulation, as long as the other active components have no adverse effect on the desired effect of the mesenchymal stem cell extract.

For example, when the skin care product, cosmetic or medicament for reducing wrinkles is manufactured, a suitable amount of an emulsifier, a perfume and other active components of reducing wrinkles can be added. The active components can be hyaluronic acid, elastin, collagen, reticulin, and/or trophic factors (such as BMP-7, SDF-1, VEGF, CXCR4, BDNF and IL-17), etc.

When the skin care product, cosmetic or medicament manufactured by the use of the mesenchymal stem cell extract of the present invention is administered to the skin surface in the form for external use, the skin surface can be heated with a heating means prior to, simultaneously with, and/or after the administration of the skin care product, cosmetic or medicament, to increase the skin temperature to a temperature of 38° C. or higher, but not harmful to the skin. For example, (i) the skin care product, cosmetic or medicament of the present invention may be applied or sprayed onto the skin surface and then the skin surface is heated immediately; (ii) the skin care product, cosmetic or medicament of the present invention may be applied or sprayed onto the skin surface for 15 to 30 minutes, and then the skin surface is heated; (iii) the skin surface is heated for 3 to 5 minutes, and then the skin care product, cosmetic or medicament of the present invention is applied or sprayed onto the skin surface; or (iv) the skin surface is heated to appropriately increase the skin surface temperature and maintain at the increased temperature, while the skin care product, cosmetic or medicament of the present invention is applied or sprayed onto the skin surface during the heating period.

The skin surface can be heated with a contact heating means or a non-contact heating means. For example, a suitable contact heating means includes, but is not limited to applying a facial mask to the skin surface, or placing a heat pack, a hot towel, a heating pad, or a heating plate on the skin surface, to appropriately increase the skin temperature through the use of the facial mask, heating pack, hot towel, heating pad, or a heating plate. A suitable non-contact heating means includes the use of a steam engine (such as beauty making ion steamer) and a heating lamp, to heat the skin surface and increase the skin temperature by hot steam released from a steam machine or light irradiated from a heating lamp.

In some embodiments of the present invention, a heating pad was used to increase the skin surface temperature by a contact heating means. The heating operation shall heat the skin surface to a temperature harmless to the skin, for example, a temperature of about 38° C. or a higher suitable temperature ranging from such as 38° C. to 50° C. In some embodiments of the present invention, the skin surface temperature was increased to about 39° C. and maintained for about 1 to 2 hours.

In the present invention, because the mesenchymal stem cell extract is used and the effective components contained therein are directly utilized to provide the desired effect, the usage amount of the mesenchymal stem cell extract can be controlled more easily, and this is different from the traditional stem cell therapy that provides the desired effect by applying living cells to secrete the effective components in a subject. Depending on the requirements of the subject, the skin care product, cosmetic or medicament manufactured by the mesenchymal stem cell extract of the present invention can be applied with various administration frequencies, such as once a day, several times a day or once for several days, etc. For example, when applying to the skin surface for repairing skin aging, the dosage of the skin care product, cosmetic or medicament may range from about 0.01 ml (as the mesenchymal stem cell extract)/cm$^2$ to about 1 ml (as the mesenchymal stem cell extract)/cm$^2$ per day, and preferably from about 0.05 ml (as the mesenchymal stem cell extract)/cm$^2$ to about 0.5 ml (as the mesenchymal stem cell extract)/cm$^2$ per day, wherein the unit "ml/cm$^2$" refers to the dosage required per cm$^2$-surface area of the treated subject. However, for subjects with more severe skin aging conditions, the dosage can be increased to several times or several tens of times, depending on the practical requirements. In an embodiment of using the mesenchymal stem cell extract of the present invention for repairing skin aging, the dosage of the skin care product, cosmetic or medicament is about 0.1 ml (as the mesenchymal stem cell extract)/cm$^2$ per day.

The present invention also provides a kit, comprising (1) a heating tool, and (2) a mesenchymal stem cell extract. The selection of the heating tool is in line with the above descriptions for heating, and the selection of the mesenchymal stem cell extract and the form and dosage for administering thereof are all in line with the above descriptions.

In addition, the present invention also provides a method for repairing skin aging in a subject in need, comprising administering to the subject an effective amount of a mesenchymal stem cell extract. The selection of the mesenchymal stem cell extract and the form and dosage for administrating thereof are all in line with the above descriptions.

The present invention will be further illustrated in detail with specific examples as follows. However, the following examples are provided only for illustrating the present invention, and the scope of the present invention is not limited thereby.

EXAMPLES

Example 1

Separation and Culture of Mesenchymal Stem Cells (1) Mesenchymal Stem Cells were Separated from the Tissues Fat tissues (NR0, NR1, NR2, NR3, NR4, AD03, AD61, BN08 and MS14) separated from different human body were cut into small pieces (about 0.5 cm×0.5 cm) by using an operating scissors. The cut fat tissues were placed in a 50 ml tube, washed with 25 ml of 1× phosphate buffered saline (PBS, containing 2% penicillin-streptomycin), and then centrifuged (room temperature, 400 g, 5 minutes). The supernatant was removed. The tissues were washed with 25 ml of 1× PBS (containing 2% penicillin-streptomycin) and centrifuged (room temperature, 300 g, 5 minutes). The supernatant was removed and 20 ml of 1× PBS (containing 0.4 mg/ml collagenase type IV (Invitrogen)) was added into the tube. The tube was placed into a shaker and shaken for 1 hour (37° C., 40 rpm) until the collagenase type IV reacted completely with the fat tissues, and then the fat tissues were centrifuged (room temperature, 400 g, 5 minutes). The supernatant and the tissue scraps were removed. The remains are stromal vascular fractions (SVFs) that include a great amount of mesenchymal stem cells. The SVF was washed with 20 ml of 1× PBS (containing 2% penicillin-streptomycin) and centrifuged (room temperature, 300 g, 5 minutes). The supernatant was removed. The SVF was washed with 10 ml of 1× PBS (containing 2% penicillin-streptomycin) and centrifuged (room temperature, 300 g, 5 minutes). The supernatant was removed. The mesenchymal stem cells were collected and cultured by the steps as shown in the following Experiment (2).

The above manufacturing processes were repeated, but the fat tissue was substituted with umbilical cord or bone marrow, respectively, to obtain a SVF that is separated from umbilical cord or bone marrow.

(2) Culture of Mesenchymal Stem Cells

The keratinocyte-serum free medium (K-SFM, Gibco) was used as a basal medium [added with 5% fetal *bovine* serum (FBS, Hyclone), 25 mg of *bovine* pituitary extract (BPE, Gibco), 2.5 µg of recombinant epidermal growth factor (Gibco), 2 mM N-acetyl-L-cysteine (Sigma), 0.2 mM L-ascorbic acid 2-phosphate (Sigma), and 1% penicillin-streptomycin (Biowest)] to resuspend the SVF obtained from the Experiment (1) in a flask. Recombinant epidermal growth factor (EGF), B27, biotinylated epithelial growth factor (BEGF) or heparin could be added to the basal medium and then left to sit in an incubator (37° C., 5% $CO_2$) to amplify the amount of mesenchymal stem cells for use in the following examples.

Example 2

Analysis of the Trophic Factors in Mesenchymal Stem Cells (1) Preparation of Total RNA of the Mesenchymal Stem Cells The mesenchymal stem cells provided by Example 1 were washed with 0.1 mM PBS once, completely mixed with 350

µl of a RLT buffer (containing 1% β-mercaptoethanol, QIAGEN, CA, USA), and then completely mixed with an equal volume (i.e., 350 µl) of 70% alcohol. The mixture was transferred into an RNeasy mini column (QIAGEN, CA, USA) and centrifuged (12000 rpm, 15 seconds). The supernatant was removed and 700 µl of a RW1 buffer (QIAGEN, CA, USA) was added. The mixture was centrifuged (12000 rpm, 15 seconds). The supernatant was removed and 500 µl of a RPE buffer (QIAGEN, CA, USA) was added. The mixture was centrifuged (12000 rpm, 15 seconds). The supernatant was removed and 500 µl of the RPE buffer was added once again. The mixture was centrifuged (12000 rpm, 1 minute) to exclude the residual reagent. The RNeasy mini column was transferred into a 1.5 ml microtube. 30 µl RNase free water (QIAGEN, CA, USA) was added onto the center of the membrane of RNeasy mini column and left to sit for 5 minutes. The RNeasy mini column and 1.5 ml microtube were centrifuged (12000 rpm, 1 minute), and the eluted filtrate (i.e., the total RNA of the mesenchymal stem cells) was collected. Then, the absorbance of the filtrate at a wavelength of 260 nm was determined by a spectrophotometer (DU-800, Beckman) to evaluate the concentration of RNA. Then, the RNA was stored at −80° C. and used for the following revere transcription polymerase chain reaction and gel analysis.

(2) Reverse Transcription Polymerase Chain Reaction (RT-PCR)

The total RNA provided by the above experiment (1) was reverse transcribed into cDNA. 2.5 µl of each primer (10 pM) shown in Table 1A, 7.5 µl ddH$_2$O, and 12.5 µl of EconoTaq® PLUS GREEN 2× Master Mix (Lucigen, Middleton, Wis., USA) were mixed with 2.5 µl of the cDNA. The mixture was placed in a RT-PCR machine. The reaction conditions were set as follows: i) 94° C. for 30 seconds, 55° C. for 30 seconds, and 94° C. for 60 seconds, with 30 cycles of the aforesaid steps; ii) 72° C. for 10 minutes; and iii) cooling to 4° C. to stop the reaction. The obtained RT-PCR product was analyzed by electrophoresis for 30 minutes through a 1.5% agarose gel (voltage: 100 volt (V)). Then, the gel was placed in and stained with ethidium bromide for 10 minutes, and photographed by a gel image capture system (DOC PRINT DP-001FDC, VilberLourmat France). The results are shown in FIG. 1. The expression levels of genes were quantified by a software, Image J. The results are shown in Table 1B.

TABLE 1A

| Name | Nucleic acid sequence of primer | Number of sequence |
|---|---|---|
| BMP-7 | Forward: GGCTGGCAGCACTGGATCAT | 1 |
|  | Reverse: ACCAGCGTCTGCACGATGGC | 2 |
| SDF1 | Forward: ATGAACGCCAAGGTCGTGGTC | 3 |
|  | Reverse: CTTGTTTAAAGCTTTCTCCAGGTACT | 4 |
| CXCR4 | Forward: GGCCCTCAAGACCACAGTCA | 5 |
|  | Reverse: TTAGCTGGAGTGAAAACTTGAAG | 6 |
| IL-17 | Forward: TCCACCGCAATGAGGACCCTG | 7 |
|  | Reverse: TGACACAGGTGCAGCCCACG | 8 |
| β-actin | Forward: CGCCAACCGCGAGAAGAT | 9 |
|  | Reverse: CGTCACCGGGAGTCCATCA | 10 |

TABLE 1B

|  | BMP-7 | SDF1 | CXCR4 | IL-17 | β-actin |
|---|---|---|---|---|---|
| NR0 | 6481.154 | 6602.347 | 6299.083 | 6995.619 | 8781.548 |
| NR1 | 6070.497 | 3925.376 | 7827.69 | 7670.841 | 8680.669 |
| NR2 | 2733.012 | 4615.518 | 3772.983 | 5141.184 | 8319.719 |
| NR3 | 3047.426 | 4496.962 | 7202.548 | 7364.548 | 11040.55 |
| NR4 | 3650.841 | 5452.154 | 8289.619 | 7027.841 | 10298.08 |
| BMSC | 3380.013 | 7032.962 | 5809.719 | 5499.376 | 11278.72 |
| WJ | 158.092 | 7183.376 | 2600.719 | 2794.355 | 8377.79 |
| AD03 | 8368.326 | 6174.083 | 8144.962 | 7924.719 | 9489.376 |
| AD61 | 2632.376 | 4142.912 | 4682.77 | 4944.598 | 9732.719 |
| BN08 | 3286.619 | 3696.912 | 7450.548 | 7189.669 | 10796.48 |
| MS14 | 3567.719 | 5559.489 | 6064.012 | 6903.782 | 10801.45 |

As shown in FIG. 1 and Table 1B, the gene expression of trophic factors can be detected in the total RNA of the mesenchymal stem cells originated from fat tissue (i.e., NR0, NR1, NR2, NR3, NR4, AD03, AD61, BN08 and MS14), bone marrow and Wharton's jelly (WJ). The expression level of β-actin was served as an internal control. The expression levels of trophic factors such as BMP-7, SDF-1, CXCR4, IL-17, etc. of the mesenchymal stem cells originated from the fat tissue were higher than those of the mesenchymal stem cells originated from other tissue such as umbilical cord or bone marrow. This result shows that the mesenchymal stem cells separated from an animal tissue all have an ability of secreting the aforesaid trophic factors.

Example 3

Preparation of Mesenchymal Stem Cell Extract

Mesenchymal stem cells provided by Example 1 were resuspended with typsin-EDTA. The suspension was transferred into a microtube and centrifuged (room temperature, 400 g, 5 minutes). The supernatant was removed. The previously prepared proteolysis buffer [comprising a NP40 lysis buffer (iNtron biotechnology, Korea), PMSF, a protease inhibitor, β-glycerol phosphate, and Na$_3$VO$_4$, at a ratio of 96:1:1:1:1] was added into the microtube, and then pipetted to lyse the cells. The suspension was shaken at 4° C. for 20 minutes and centrifuged (4° C., 12000 to 13000 rpm, 10 minutes). The supernatant (i.e., mesenchymal stem cell extract) was collected and used in the following examples.

Example 4

Administration of Mesenchymal Stem Cell Extract

F344 rats were separated into 3 groups with 3 rats for each group. In one group, the F344 rats were subcutaneously injected with granulocyte colony stimulating factor (GCSF) (50 µg/kg) for 3 consecutive days. The hair on the skin area to be biopsied of the rats was cut. Then, the skin area to be biopsied was heated with a heating pad to increase the temperature of the skin surface to about 39° C. and maintained for 1 hour. The mesenchymal stem cell extracts provided by the above Example 3 was applied uniformly on the skin area to be biopsied by a dosage of 0.1 ml per 1 cm square. The heating and application steps were repeated every two days for 7 consecutive days, that is called as a "heating+MSC extract" group. In another group, the same steps of the above group were carried out but only heated for 1 hour without the MSC extract; this group was called the "heating group." The group without any treatment was called as the "control group."

Example 5

Preparation and Biopsy of Skin Tissue

The tissue of the (i) control group, (ii) heating group and (iii) heating+MSC extract group provided by Example 4 were treated by the following steps. The hair on the skin area to be biopsied of the F344 rats was cut by an electric shaver. The surgical region was disinfected by 75% alcohol, and 1 cm square pieces of the skin tissue was biopsied (the biopsying depth was about 8 mm until the fat layer was reached). The biopsied sample was soaked in a fixing solution, 10% formalin solution (neutral buffered formalin, Surgipath) to keep the initial state of the proteins in the tissue, and was dehydrated by a tissue dehydration machine (Leica TP1020). First, a cassette comprising the skin tissue was put into the tissue dehydration machine, and the tissue was sequentially processed by fixation, dehydration, washing, and rinsing (irrigation of wax). The water in the tissue was replaced by paraffin after such treatment. The treating steps were as follows: treated with a 10% formalin solution for 1 hour (fixation); treated with double distilled water for 30 minutes (rinsing); treated with 80% alcohol for 1 hour (dehydration); treated with 95% alcohol for 1 hour (dehydration); treated with 95% alcohol for 1 hour (dehydration); treated with 100% alcohol for 1 hour (dehydration); treated with 100% alcohol for 1 hour (dehydration); treated with 100% alcohol for 2 hours (dehydration); treated with xylene for 1 hour (washing); treated with xylene for 2 hours (washing); treated with paraffin wax for 1 hour (rinsing); and treated with paraffin wax for 2 hours (rinsing). The dehydrated tissue was embedded with paraffin (tissue block system TBS 88, Medite) into a paraffin block and sectioned by a hand-cranked paraffin section machine (Shandon AS325, Leica, Germany). The thickness of each section ranged from 3 μm to 5 μm.

Example 6

Skin Tissue Stain and Analysis

The sections of (i) control group, (ii) heating group and (iii) heating+MSC extract group provided by Example 5 were stained and analyzed as follows.
(1) Immunohistochemistry (IHC)

Immunofluorescence (IF) stain was utilized to detect the expression of specific antigens in the tissues. The staining steps were as follows: the skin tissues were biopsied (3 μm/section); heated at 55° C. for 30 minutes; dewaxed in xylene and rehydrated in alcohol; and heated in an antigen recovery buffer solution at 121° C. for 10 minutes; the tissues were circled by a DAKO pen; soaked in a 1× PBS solution (containing 3% hydrogen peroxide) at room temperature for 10 minutes to inactivate the intrinsic reductase; washed by a rinse buffer (1× PBS+0.3% TritonX-100) once, treated with a 1× PBS solution (containing 5% FBS) for 30 minutes to block non-specific binding; washed with a rinse buffer (1× PBS+0.05% TritonX-100) once; the primary antibodies (bromodeoxyuridine (BrdU), hyaluronic acid and CD44, Abcam) diluted in an appropriate fold (1:100 to 1:200) were added to the tissue samples, and the reaction was conducted at room temperature for 2 hours or at 4° C. overnight; the tissues were washed with a rinse buffer (1× PBS+0.05% TritonX-100) 3 times; the secondary antibody diluted in an appropriate fold (1:5000) was added to the tissue samples, and the reaction was conducted at room temperature for 1 hour; the tissues were washed with a rinse buffer (1× PBS+0.05% TritonX-100) 3 times; a DAB color reagent (3,3'-Diaminobenzidine, LSAB2 Kit, DAKO, CA, USA) was added to the tissue samples for 10 minutes. A red-brown color represents a positive result, while no color represents a negative result. Then, the tissues were counter stained with a hematoxylin solution for 1 minute. Excessive hematoxylin was washed out. The tissues were soaked in tap water for 10 minutes, and dehydrated in alcohol and mounted by the mounting medium.

Figure 2A:
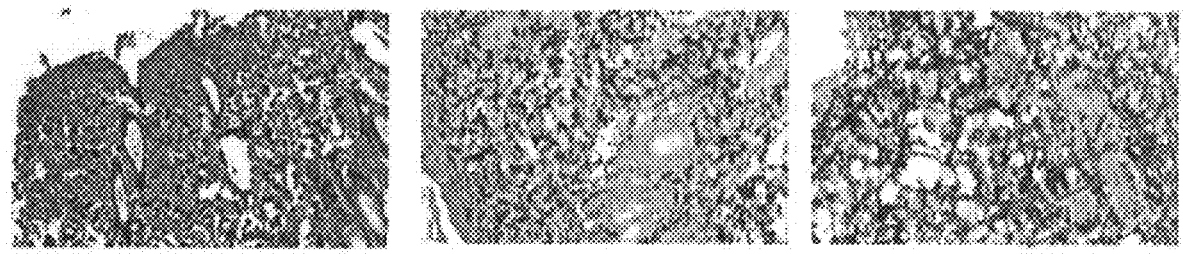
FIG. 2A is an immunohistochemistry staining picture (upper) and a statistical bar diagram (lower) showing BrdU in the skin of a rat (i) without any treatment (i.e., "control group"), (ii) after a heating treatment (i.e., "heating group"), or (iii) after a combination of a heating treatment and a treatment of mesenchymal stem cell extract (i.e., "heating+MSC extract")
Figure 2A:
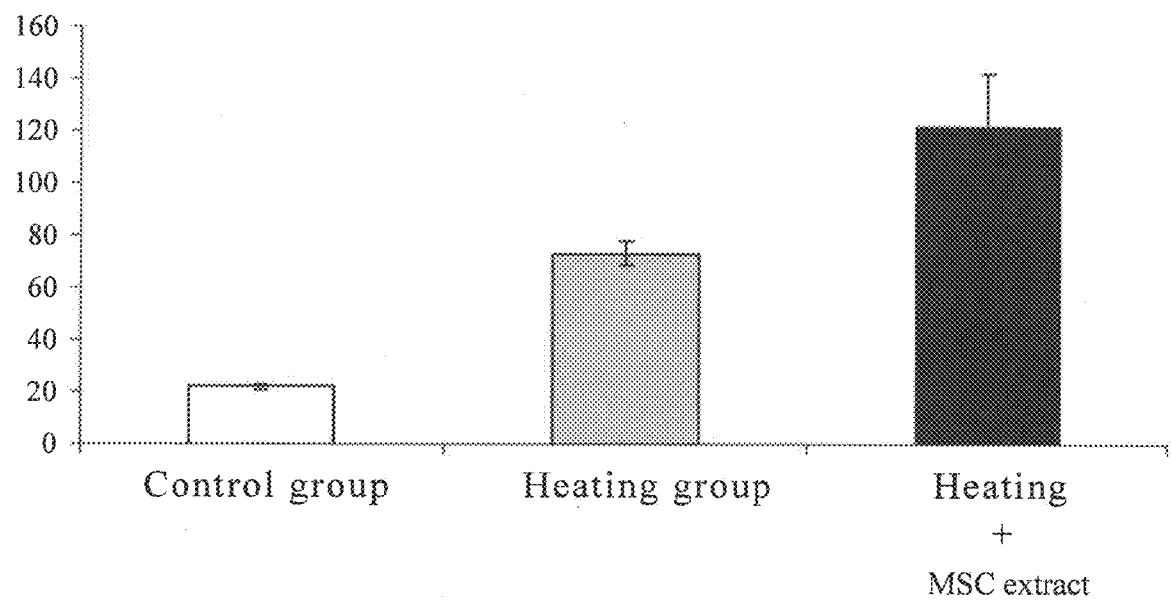
Figure 2B:
FIG. 2B is an immunohistochemistry staining picture (upper) and a statistical bar diagram (lower) showing CD34 in the skin of a rat (i) without any treatment (i.e., "control group"), (ii) after a heating treatment (i.e., "heating group"), or (iii) after a combination of a heating treatment and a treatment of mesenchymal stem cell extract (i.e., "heating+MSC extract")
Figure 2B:
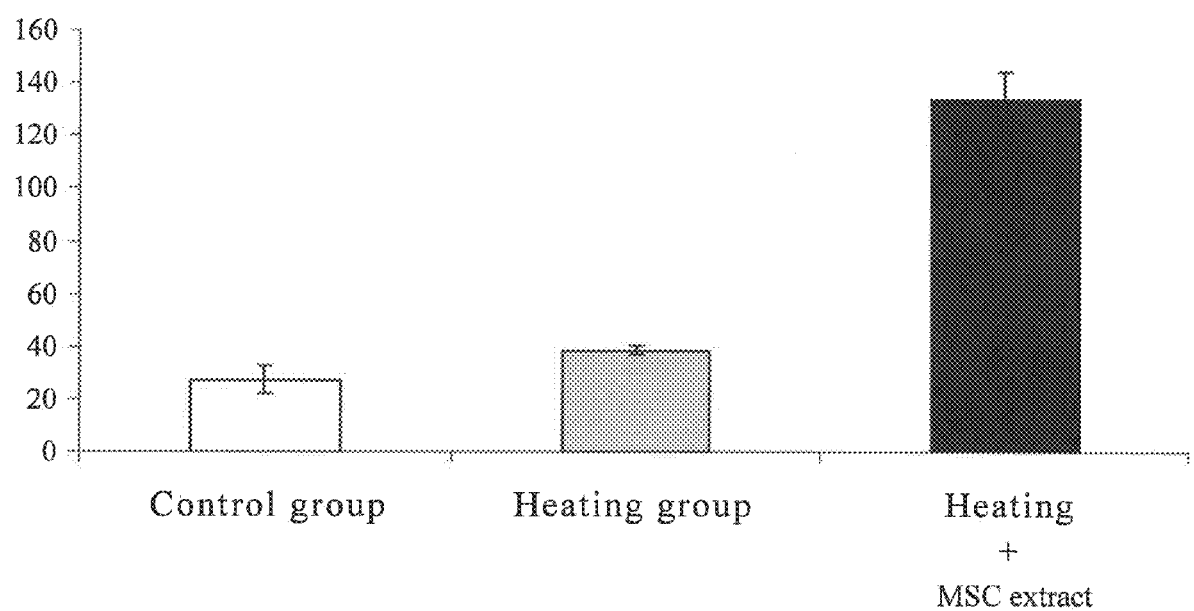
Figure 3A:
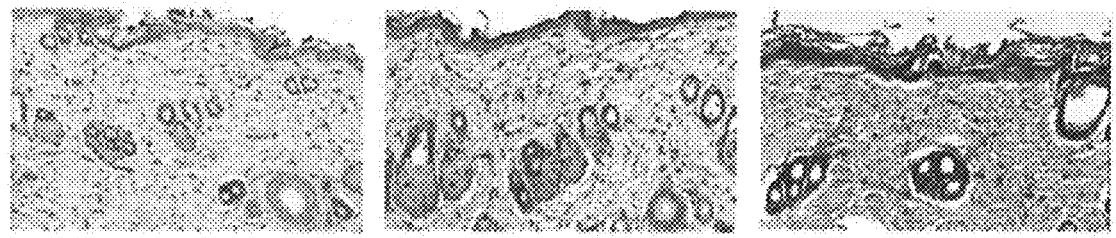
FIG. 3A is an immunohistochemistry staining picture (upper) and a statistical bar diagram (lower) showing hyaluronic acid in the skin of a rat (i) without any treatment (i.e., "control group"), (ii) after a heating treatment (i.e., "heating group"), or (iii) after a combination of a heating treatment and a treatment of mesenchymal stem cell extract (i.e., "heating+MSC extract")
Figure 3A:
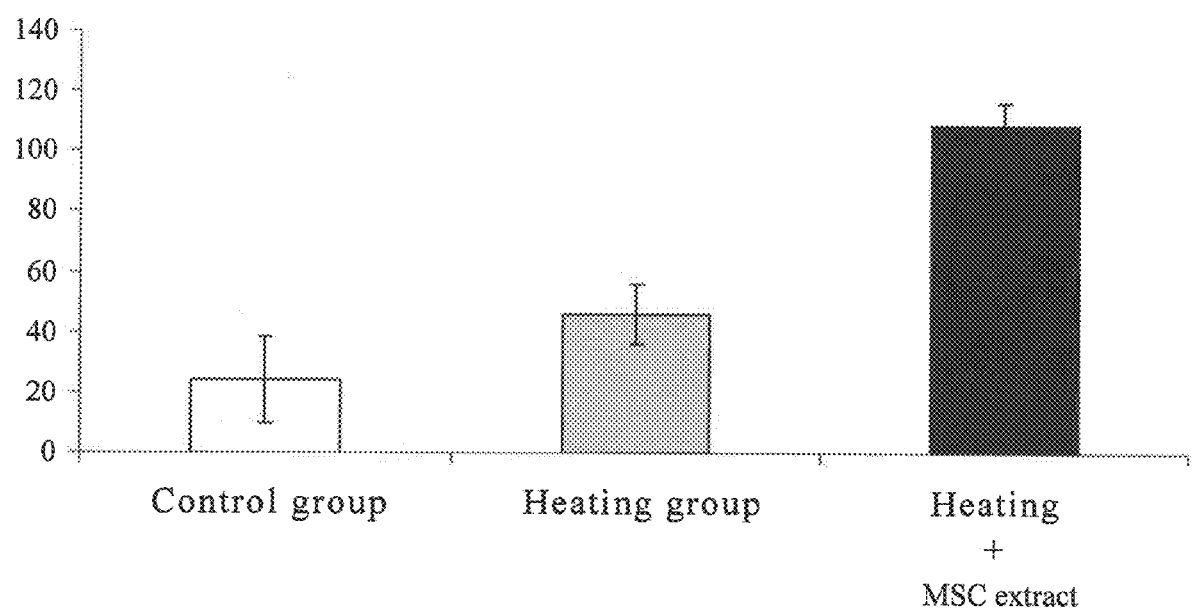

Then, the samples were dried in a hood, observed under a microscope, and recorded by a CCD digital camera system (OLYMPUS, DP70). The results are shown in FIGS. 2A, 2B, 3A and Tables 2A, 2B, 3A. FIG. 2A shows an indicator of cell proliferation (i.e., BrdU) analyzed by immunohistochemistry, FIG. 2B shows an indicator of endogenous hematopoietic progenitor cells (i.e., CD34) analyzed by immunohistochemistry, FIG. 3A shows the result of hyaluronic acid (an indicator of scar eliminating capacity) analyzed by immunohistochemistry, and Tables 2A, 2B, 3A show the quantitative results of FIGS. 2A, 2B, 3A respectively.
(2) Masson's Trichrome Stain/Gelatinous Fiber Stain Masson's trichrome stain/gelatinous fiber stain is a histochemistry stain, which can be used to identify collagen fiber. In an acidic environment, it can selectively stain collagen fibers and muscle fibers. After the collagen fiber was treated by an acid, the Biobrich Scarlet leaked out from collagen and turned into blue when stained with aniline blue. The staining steps were as follows: the sections were dewaxed, soaked in a Bouin's solution at 56° C. for 1 hour, stained in a hematoxylin solution for 5 minutes (nucleus staining); washed by running water for 15 minutes and sequentially stained with Biebrich Scarlet-Acid fuchsin (Sigma, HT15-1) for 15 minutes, stained with phosphomolybdic acid-phosphotungstic acid (Sigma, P7390 and P4006) for 15 minutes, stained with aniline blue for 5 minutes, soaked in 1% ice-cold acetic acid for 5 minutes, and dehydrated in alcohol and mounted by a mounting medium.

Figure 3B:
FIG. 3B is a Masson's trichrome staining picture (upper) and a statistical bar diagram (lower) showing collagen in the skin of a rat (i) without any treatment (i.e., "control group"), (ii) after a heating treatment (i.e., "heating group"), or (iii) after a combination of a heating treatment and a treatment of mesenchymal stem cell extract (i.e., "heating+MSC extract")
Figure 3B:
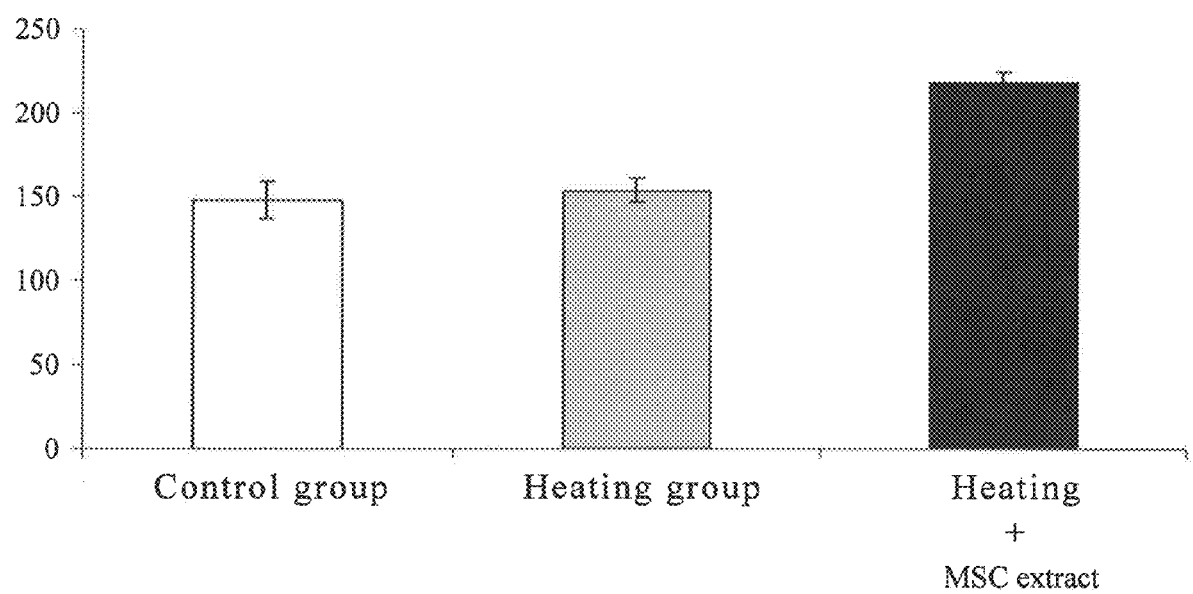

Then, the samples were dried in a hood for 1 day, observed under a microscope, and recorded by a CCD digital camera system (OLYMPUS, DP70). The results are shown in FIG. 3B and Table 3B. FIG. 3B shows the result of collagen (an indicator of skin aging, wherein a less amount of collagen represents a higher level of aging) analyzed by Masson's trichrome stain/gelatinous fiber stain. Table 3B shows the quantitative results of FIG. 3B.
(3) Elastic Stain (Modified Verhoff's) and Reticular Stain This staining method is utilized to identify elastin and reticulin, wherein the stained elastin and reticulin turn into blue-black. The staining steps are as follows: the skin tissue was biopsied (3 μm/section); heated at 55° C. for 30 minutes; dewaxed in xylene and rehydrated in alcohol; stained with a working elastic stain solution for 15 minutes; washed by running water for 1 minute; stained with a 2% Ferric chloride differentiating solution for 20 seconds; washed by running water for 1 minute; stained with a 5% sodium thiosulfate solution for 1 minute; washed by running water for 1 minute; stained with a Van Gieson's solution for 3 minutes; and dehydrated in alcohol and mounted by a mounting medium.

Figure 3C:
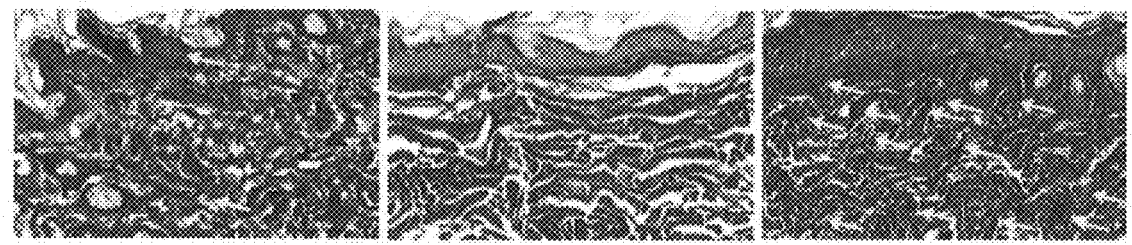
FIG. 3C is an elastic and reticular staining picture (upper) and a statistical bar diagram (lower) showing elastin in the skin of a rat (i) without any treatment (i.e., "control group"), (ii) after a heating treatment (i.e., "heating group"), or (iii) after a combination of a heating treatment and a treatment of mesenchymal stem cell extract (i.e., "heating+MSC extract")
Figure 3C:
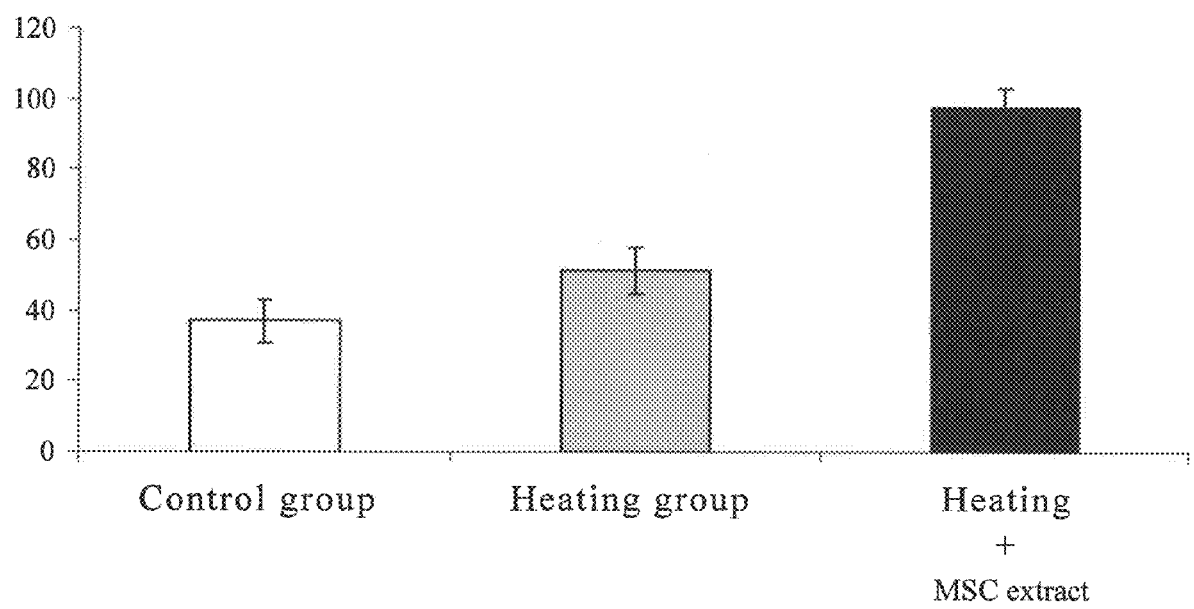
Figure 3D:
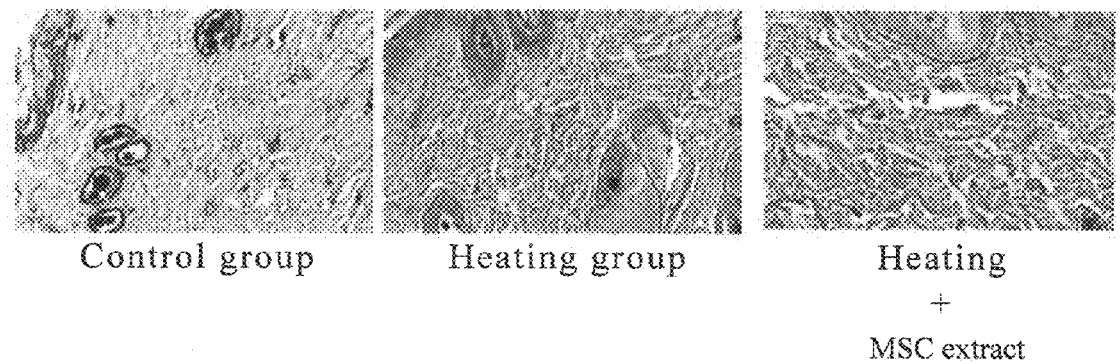
FIG. 3D is an elastic and reticular staining picture (upper) and a statistical bar diagram (lower) showing reticulin in the skin of a rat (i) without any treatment (i.e., "control group"), (ii) after a heating treatment (i.e., "heating group"), or (iii) after a combination of a heating treatment and a treatment of mesenchymal stem cell extract (i.e., "heating+MSC extract").
Figure 3D:
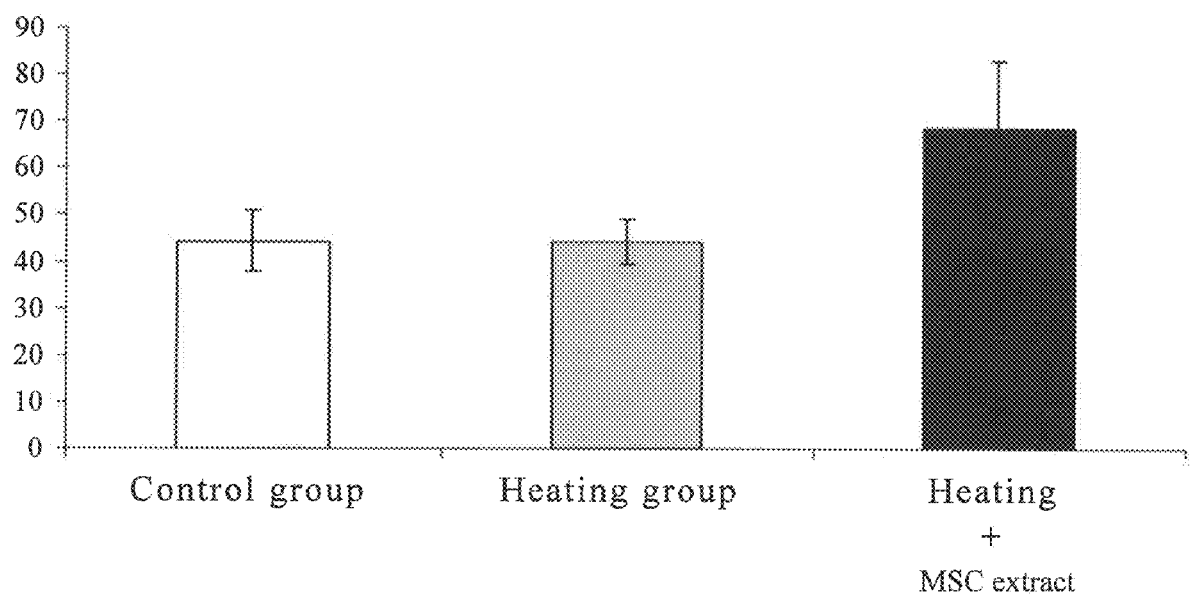

Then, the samples were dried in a hood for 1 day, observed under a microscope, and recorded by a CCD digital camera system (OLYMPUS, DP70). The results are shown in FIGS. 3C and 3D and Tables 3C and 3D. FIG. 3C shows the result of elastin (an indicator of skin elasticity) analyzed by elastic stain and reticular stain, FIG. 3D shows the result of reticulin (an indicator of skin elasticity) analyzed by elastic stain and reticular stain, and Tables 3C and 3D show the quantitative results of FIGS. 3C and 3D respectively.

(4) The Results (4-1) Mesenchymal Stem Cell Extract can Stimulate Cell Proliferation at the Administered Region and Stimulate Endogenous Hematopoietic Progenitor Cells to Gather and Proliferate at the Administered Region FIGS. 2A and 2B show the indicator of cell proliferation (i.e., BrdU) and the indicator of endogenous hematopoietic progenitor cells (i.e., CD34) in the skin of a rat without any treatment or with different treatment analyzed by immunohistochemistry, respectively. Tables 2A and 2B show the quantitative results of FIGS. 2A and 2B respectively.

TABLE 2A

| | BrdU | | |
|---|---|---|---|
| | Control group | Heating group | Heating + ESC extract |
| Average score (0 to 300) | 21.95 | 73.12 | 121.64 |

TABLE 2B

| | CD34 | | |
|---|---|---|---|
| | Control group | Heating group | Heating + ESC extract |
| Average score (0 to 300) | 27.12 | 38.67 | 133.43 |

In FIG. 2A, cells labeled with BrdU were indicated by red arrows. The result of FIG. 2A indicates that there is no BrdU-labeled cells can be observed in the "control group" without any treatment, and the increment of BrdU-labeled cells number were slight in the "heating group" with a heating treatment, but significant in the "heating+ESC extract group" with a heating treatment combined with a treatment of mesenchymal stem cell extract. As shown in FIG. 2A and Table 2A, a combination of the treatment of mesenchymal stem cell extract and a heating treatment can effectively stimulate cell proliferation of the skin tissue.

It also been observed in FIG. 2A that cell proliferation around the hair follicles of the "control group" could be almost ignored, while the proliferated cells would gather in the hair follicles of the "heating+ESC extract group" with a heating treatment combined with a treatment of mesenchymal stem cell extract" in large numbers. As the number of the cells in the brown of a single follicle, the ratio of "control group" and "heating+ESC extract group" was 1:35. The results show that the mesenchymal stem cell extract of the present invention is also helpful in reducing hair loss, promote the activation of hair follicles, promote the proliferation of hair follicle cells, and promote hair growth.

As shown in FIGS. 2A and 2B, as compared to the result in the "control group" and "heating group," the results of "heating+ESC extract group" shows that after a combination of a treatment of mesenchymal stem cell extract and a heating treatment, the number of CD34-labeled endogenous hematopoietic progenitor cells was increased significantly (red arrows in FIG. 2B indicate the sites that endogenous hematopoietic progenitor cells gathered). The results illustrate that a combination of a treatment of mesenchymal stem cell extract and a heating treatment can effectively stimulate endogenous hematopoietic progenitor cells to gather and proliferate at the administered region.

(4-2) Mesenchymal Stem Cell Extract can Promote the Expression of Hyaluronic Acid (HA), Elastin, Collagen, and Reticulin FIG. 3A shows the results of hyaluronic acid (an indicator of scar eliminating capacity) analyzed by immunohistochemistry, and Table 3A shows the quantitative results of FIG. 3A.

TABLE 3A

| | Hyaluronic acid | | |
|---|---|---|---|
| | Control group | Heating group | Heating + ESC extract |
| Average score (0 to 300) | 24.19 | 45.98 | 108.73 |

As shown in FIG. 3A and Table 3A, as compared to the result of "control group" and "heating group," the results of "heating+ESC extract group" show that after a combination of a treatment of mesenchymal stem cell extract and a heating treatment, the expression of hyaluronic acid was increased significantly (such as the red arrows in FIG. 3A). The results illustrate that the mesenchymal stem cell extract of the present invention can effectively promote the expression of hyaluronic acid.

FIG. 3B shows the results of collagen (an indicator of skin aging in which the smaller amount of collagen, the higher level of aging) analyzed by Masson's trichrome stain/gelatinous fiber stain. Table 3B shows the quantitative results of FIG. 3B.

TABLE 3B

| | Collagen | | |
|---|---|---|---|
| | Control group | Heating group | Heating + ESC extract |
| Average score (0 to 300) | 147.76 | 153.52 | 218.01 |

As shown in FIG. 3B and Table 3B, as compared to the result of "control group" and "heating group," the results of "heating+ESC extract group" show that after a combination of a treatment of mesenchymal stem cell extract and a heating treatment, the expression of collagen was increased significantly (see the blue region in FIG. 3B). The results illustrate that the mesenchymal stem cell extract of the present invention can effectively promote the expression of collagen.

FIG. 3C shows the results of elastin (an indicator of skin elasticity) analyzed by elastic stain and reticular stain, and Table 3C shows the quantitative results of FIG. 3C.

TABLE 3C

| | Elastin | | |
|---|---|---|---|
| | Control group | Heating group | Heating + ESC extract |
| Average score (0 to 300) | 37.00 | 51.33 | 97.67 |

As shown in FIG. 3C and Table 3C, as compared to the result of "control group" and "heating group," the results of "heating+ESC extract group" shows that after a combination of a treatment of mesenchymal stem cell extract and a heating treatment, the expression of elastin was increased significantly (see the yellow arrows in FIG. 3C). The results illustrate that the mesenchymal stem cell extract of the present invention can effectively promote the expression of elastin.

FIG. 3D shows the results of reticulin (an indicator of skin elasticity) analyzed by elastic stain and reticular stain, and Table 3D shows the quantitative results of FIG. 3D.

TABLE 3D

| | reticulin | | |
|---|---|---|---|
| | Control group | Heating group | Heating + ESC extract |
| Average score (0 to 300) | 44.33 | 44.33 | 68.67 |

As shown in FIG. 3D and Table 3D, as compared to the result of "control group" and "heating group," the results of "heating+ESC extract group" show that after a combination of a treatment of mesenchymal stem cell extract and a heating treatment, the expression of reticulin was increased significantly (see the yellow arrows in FIG. 3D). The results illustrate that mesenchymal stem cell extract of the present invention can effectively promote the expression of reticulin.

The above examples show that in respect to the biochemical function, the mesenchymal stem cell extract of the present invention can promote the expression of hyaluronic acid, elastin, collagen and/or reticulin in the skin. In respect to the physiological effect, it can improve skin firmness, improve skin fullness, promote skin metabolism, and improve skin structure (including thinning the skin epidermis and increasing the elasticity of the dermis). Through the aforesaid mechanisms, the mesenchymal stem cell extract of the present invention can achieve the effects of repairing skin aging, such as reducing the stripes on the skin, reducing wrinkles, preventing wrinkles, reducing the discoloration of skin, thereby, improving the appearance of the skin, etc.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A mesenchymal stem cell extract, which is a supernatant provided by the following steps:
   (1) mixing mesenchymal stem cells separated from an animal fat tissue with a proteolysis buffer containing NP40 lysis buffer, phenylmethanesulfonyl fluoride (PMSF), a protease inhibitor, β-glycerol phosphate and $Na_3VO_4$, to lyse the cells and provide a cell lysate; and
   (2) centrifuging the cell lysate at a temperature of no more than 4° C. to collect the supernatant,
   wherein the supernatant obtained from step (2) consists of bone morphogenetic protein-7 (BMP-7), stromal cell-derived factor-1 (SDF-1), vascular endothelial growth factor (VEGF), C-X-C chemokine receptor type-4 (CXCR4), brain-derived neurotrophic factor (BDNF), interleukin-17 (IL-17), other cytoplasmic ingredients and components of the proteolysis buffer.

2. The mesenchymal stem cell extract as claimed in claim 1, which is provided as an emulsion, a cream, a gel, a paste, a spray or a solution.

3. The mesenchymal stem cell extract as claimed in claim 2, wherein the gel is an aquagel.

4. The mesenchymal stem cell extract as claimed in claim 2, wherein the paste is a dispersing paste or an ointment.

5. The mesenchymal stem cell extract as claimed in claim 2, wherein the solution is a washing fluid or a suspension.

* * * * *